United States Patent
Hwang et al.

(10) Patent No.: US 11,351,172 B2
(45) Date of Patent: Jun. 7, 2022

(54) PHARMACEUTICAL COMPOSITION AND USE FOR APPLYING RIBOCICLIB IN PHOSPHODIESTERASE 4-MEDIATED DISEASE TREATMENT OF PATIENT AND INHIBITION OF PHOSPHODIESTERASE 4 ACTIVITY

(71) Applicant: Chang Gung University, Taoyuan (TW)

(72) Inventors: Tsong-Long Hwang, Taoyuan (TW); Po-Jen Chen, Taoyuan (TW)

(73) Assignee: CHANG GUNG UNIVERSITY, Taoyuan (TW)

( * ) Notice: Subject to any disclaimer, the term of this patent is extended or adjusted under 35 U.S.C. 154(b) by 93 days.

(21) Appl. No.: 16/793,275

(22) Filed: Feb. 18, 2020

(65) Prior Publication Data
US 2020/0397789 A1 Dec. 24, 2020

(30) Foreign Application Priority Data
Jun. 21, 2019 (TW) ................. 108121743

(51) Int. Cl.
*A61K 31/519* (2006.01)
*A61P 11/00* (2006.01)

(52) U.S. Cl.
CPC ............ *A61K 31/519* (2013.01); *A61P 11/00* (2018.01)

(58) Field of Classification Search
CPC ............................. A61K 31/519; A61P 11/00
See application file for complete search history.

(56) References Cited

FOREIGN PATENT DOCUMENTS

| EP | 3156406 A1 | 4/2017 | |
| WO | WO-2018073687 A1 * | 4/2018 | ........... A61K 31/519 |

OTHER PUBLICATIONS

PrKISQALI™ (ribociclib tablets), Product Monograph Including Patient Medication Information, https://pdf.hres.ca/dpd_pm/00044564.PDF, Date of Revision Mar. 19, 2018, 48 pages.
Office Action issued by Taiwan Intellectual Property Office in TW application No. 108121743 dated May 6, 2021 (5 pages).
Office Action issued by CNIPA in CN application No. 202010078474.3 dated May 7, 2021 (8 pages).
Zheng, X.-Y. et al., "Changes of Phosphodiesterase 4 Activity in Lung Tissue of Acute Lung Injury Model in Rats," Chinese Pharmacological Bulletin 22(7):844-848, Jul. 2006, with English abstract (2 pages).
Konrad, Franziska M. et al., "The Unrecognized Effects of Phosphodiesterase 4 on Epithelial Cells in Pulmonary," (2015) Inflammation. PLoS One 10(4): e0121725 (25 pages).
Ribnikar, Domen et al., "Targeting CDK4/6 pathways and beyond in breast cancer," The Breast 43 (2019) pp. 8-17 (10 pages).

* cited by examiner

*Primary Examiner* — Sarah Pihonak
(74) *Attorney, Agent, or Firm* — Muncy, Geissler, Olds & Lowe, P.C.

(57) ABSTRACT

The invention provides a pharmaceutical composition for treating phosphodiesterase 4-mediated (PDE4-mediated) disease in a patient and inhibition of phosphodiesterase 4 (PDE4) activity. The pharmaceutical composition includes an effective amount of Ribociclib and a pharmaceutically acceptable carrier. The invention further provides a use of the pharmaceutical composition for treating PDE4-mediated disease in a patient. The application of the pharmaceutical composition of the present invention and use thereof are advantageous for inhibiting of PDE4 activity and thus treating a PDE4-mediated disease.

3 Claims, 6 Drawing Sheets

PHARMACEUTICAL COMPOSITION AND USE FOR APPLYING RIBOCICLIB IN PHOSPHODIESTERASE 4-MEDIATED DISEASE TREATMENT OF PATIENT AND INHIBITION OF PHOSPHODIESTERASE 4 ACTIVITY

CROSS REFERENCE TO RELATED APPLICATIONS

This Non-provisional application claims priority under 35 U.S.C. § 119(a) on Patent Application No(s). 108121743 filed in Taiwan, Republic of China on Jun. 21, 2019, the entire contents of which are hereby incorporated by reference.

BACKGROUND OF THE INVENTION

Field of Invention

The invention relates to a pharmaceutical composition for treating a patient with phosphodiesterase 4-mediated disease and inhibiting phosphodiesterase 4 activity and use thereof.

Related Art

Phosphodiesterase (PDE) family can hydrolyze cyclic adenosine monophosphate (cAMP) and cyclic guanosine monophosphate (cGMP) to AMP and GMP, and thus inactivated them. In the said family, the phosphodiesterase 4 is a specific enzyme for cAMP. The phosphodiesterase 4 is ubiquitously present in inflammation and immune cells.

cAMP is a critical second messenger in the cells. It is known that increased concentration of cAMP can inhibit pro-inflammatory responses in various types of inflammatory and immune cells, including lymphocytes, monocytes, macrophages, neutrophils, eosinophils, basophils, and the lung epithelial cells and so on.

However, phosphodiesterase 4 (PDE4) may reduce the concentration of cAMP, which may reduce its effect on inhibiting various types of inflammation and proinflammatory response in immune cells, and thus leading to cause inflammatory diseases and allergic diseases easily. It is currently known that increased activity of PDE4 is associated with certain inflammatory diseases or allergic diseases, such as asthma, chronic bronchitis, emphysema, atopic dermatitis, urticaria, allergic rhinitis, allergic conjunctivitis, psoriasis, rheumatoid arthritis, chronic obstructive pulmonary disease (COPD), acute respiratory distress syndrome, multiple sclerosis and so on.

Accordingly, it is an urgent need to provide a pharmaceutical composition for inhibiting PDE4 activity and use thereof. The pharmaceutical composition can reduce PDE4 activity in a patient for avoiding the effect of PDE4 to the function of the immune system, and thus achieves the efficacy of treating the diseases related to the PDE4 activity.

SUMMARY OF THE INVENTION

In view of the foregoing objectives, a purpose of the invention is to provide a pharmaceutical composition for inhibiting PDE4 activity and use thereof. The pharmaceutical composition can reduce PDE4 activity in an individual for avoiding the effect of PDE4 to the function of the immune system, and thus achieves the efficacy of treating phosphodiesterase 4-mediated (PDE4-mediated) diseases.

To achieve the above objective, the invention provides a pharmaceutical composition for treating a phosphodiesterase 4-mediated (PDE4-mediated) disease in a patient. The pharmaceutical composition comprises an effective amount of Ribociclib and a pharmaceutically acceptable carrier.

To achieve the above objective, the invention also provides a pharmaceutical composition for use in the treatment of a PDE4-mediated disease in a patient, wherein the pharmaceutical composition comprises an effective amount of Ribociclib and a pharmaceutically acceptable carrier.

To achieve the above objective, the invention further provides a pharmaceutical composition for inhibiting PDE4 activity. The pharmaceutical composition comprises an effective amount of Ribociclib and a pharmaceutically acceptable carrier.

To achieve the above objective, the invention further provides a method for treating a PDE4-mediated disease in a patient. The method comprises a step of providing a pharmaceutical composition to the patient. The pharmaceutical composition comprises an effective amount of Ribociclib and a pharmaceutically acceptable carrier.

In one embodiment, the PDE4-mediated disease is acute lung injury, acute respiratory distress syndrome, psoriasis, chronic obstructive pulmonary disease, pulmonary fibrosis, liver injury, fatty liver disease, liver fibrosis, myocardial infarction, shock, stroke, vasculitis, sepsis, inflammatory bowel disease, rheumatoid arthritis, systemic lupus erythematosus or atopic dermatitis.

In one embodiment, Ribociclib is used to treat the PDE4-mediated disease by inhibiting neutrophils activity.

In one embodiment, Ribociclib is used to treat the PDE4-mediated disease by inhibiting phosphodiesterase 4 (PDE4) pathway.

In one embodiment, Ribociclib is used to treat the PDE4-mediated disease by inhibiting phosphodiesterase 4A (PDE4A) activity, phosphodiesterase 4B (PDE4B) activity, phosphodiesterase 4C (PDE4C) activity or phosphodiesterase 4D (PDE4D) activity of the PDE4 pathway.

In one embodiment, the effective amount of Ribociclib is from 1 μg/kg of the body weight/per day to 100 mg/kg of the body weight/per day.

As mentioned above, the efficacy of this invention is to provide a pharmaceutical composition for inhibiting PDE4 activity and use thereof. The pharmaceutical composition can reduce PDE4 activity in a patient for avoiding the effect of PDE4 to the function of the immune system, and thus achieves the efficacy of treating PDE4-mediated diseases.

BRIEF DESCRIPTION OF THE DRAWINGS

FIGS. 1A-1F show results of PDE4 activity inhibited specifically by Ribociclib.

FIG. 3 shows the partially enlarged photos of mice skin after 0 to 5th day treated by different treatments.

FIG.4 shows the lung tissue section photos of mice treated by different treatments. The lung tissue sections were stained by H&E.

DETAILED DESCRIPTION OF THE INVENTION

The embodiments and examples of the pharmaceutical composition for inhibiting phosphodiesterase activity and the use thereof in this invention will be apparent from the following detailed description, which proceeds with reference to the accompanying figures, wherein the same references relate to the same elements.

The pharmaceutical composition of this invention and use thereof can reduce PDE4 activity in a patient for avoiding the effect of PDE4 to the function of the immune system, and thus achieves the efficacy of treating PDE4-mediated diseases.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used. It is also to be understood that the terminology used herein is for the purpose of describing particular embodiments only, and is not intended to be limiting.

As used herein, the terms "phosphodiesterase" and "PDE" refer to an enzyme which can hydrolyze phosphodiester bond. The phosphodiesterase is able to hydrolyze cAMP and cGMP to AMP and GMP, thereby inactivating them. Phosphodiesterase can be divided into 11 types (PDE1 to PDE11) according to the characteristics of amino acid sequence, matrix specificity, modulation properties, pharmacological properties and cell or tissue distribution. In the phosphodiesterase family, phosphodiesterase 4 (PDE4) is a specific enzyme for cAMP. The phosphodiesterase 4 is ubiquitously present in inflammatory and immune cells. It is currently known that increased activity of PDE4 is associated with certain inflammatory diseases or allergic diseases, such as asthma, chronic bronchitis, emphysema, atopic dermatitis, urticaria, allergic rhinitis, allergic conjunctivitis, psoriasis, rheumatoid arthritis, chronic obstructive pulmonary disease, acute respiratory distress syndrome, multiple sclerosis and so on.

The term "phosphodiesterase 4-mediated disease" or "PDE4-mediated disease" refers to the inflammatory diseases or allergic diseases that are associated with the PDE4 activity as described above. PDE4-mediated disease is, for example, but not limited to, asthma, chronic bronchitis, emphysema, atopic dermatitis, urticaria, allergic rhinitis, allergic conjunctivitis, psoriasis, rheumatoid arthritis, chronic obstructive pulmonary disease, acute respiratory distress syndrome, multiple sclerosis, acute lung injury, pulmonary fibrosis, liver injury, fatty liver disease, liver fibrosis, myocardial infarction, shock, stroke, vasculitis, sepsis, inflammatory bowel disease, or systemic lupus erythematosus.

The term "Ribociclib" is also called "LEE011", "LEE 011" and "Kisqali" which is a useful CDK4 and CDK6 selective inhibitor. The IUPAC name of Ribociclib is "7-Cyclopentyl-N,N-dimethyl-2-{[5-(1-piperazinyl)-2-pyridinyl]amino}-7H-pyrrolo[2,3-d]pyrimidine-6-carboxamide". In the USA, Ribociclib is approved for treating hormone receptor (HR)-positive and human epidermal growth factor receptor 2 (HER2)-negative breast cancer, advanced breast cancer or metastatic breast cancer. Ribociclib is combined with letrozole as initial endocrine therapy or combined with fulvestrant after the progression of disease in endocrine therapy. The drug is marketed by Novartis under the trade name Kisqali® in a dosage form of film-coated tablet containing 200 mg of Ribociclib. Ribociclib of this invention can includes the following structure, or salt, solvate, hydrate, prodrug, enantiomer, diastereoisomer, or tautomer thereof.

As used herein, a "disease" is a state of health of a subject wherein the subject cannot maintain homeostasis, and wherein if the disease is not ameliorated then the subject's health continues to deteriorate.

The terms "treat", "treating" and "treatment" as used herein, means reducing the frequency or severity with which symptoms of a disease or condition are experienced by a subject by virtue of administering an agent or pharmaceutical composition to the subject.

As used herein, the term "pharmaceutically acceptable" refers to a material, such as a carrier or diluent, which does not abrogate the biological activity or properties of Ribociclib, or any salt, solvate, hydrate, prodrug, enantiomer, diastereoisomer, or tautomer thereof useful within the invention, and is relatively non-toxic, i.e., Ribociclib may be administered to a subject without causing undesirable biological effects or interacting in a deleterious manner with any of the components of the composition in which it is contained.

As used herein, the term "pharmaceutically acceptable carrier" means a pharmaceutically acceptable salts, material, composition or carrier, such as a liquid or solid filler, diluent, excipient, solvent or encapsulating material, involved in carrying or transporting Ribociclib of the invention within or to the subject such that Ribociclib may perform its intended function. Typically, Ribociclib is carried or transported from one organ or portion of the body to another organ or portion of the body. Each salt or carrier must be compatible with the other ingredients of the formulation, including Ribociclib useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agents; lubricating agent; binding agents; disintegrating agents; wetting agents; emulsifying agents; coloring substances; releasing agents; coating agents; sweetening agents; flavoring agents; aromatic agents; preservatives; antioxidants; plasticizers; gelling agents; thickening agents; hardening agents; setting agents; suspending agents; surface active agents; humectant; carriers; stabilizers; and other non-toxic compatible substances employed in pharmaceutical formulations.

Pharmaceutical compositions that are useful in the methods of the invention may be suitably developed for nasal, inhalational, oral, rectal, vaginal, pleural, peritoneal, parenteral, topical, transdermal, pulmonary, intranasal, buccal, ophthalmic, epidural, intrathecal, intravenous or another route of administration. Other contemplated formulations include projected nanoparticles, microspheres, liposomal preparations, coated particles, polymer conjugates, resealed erythrocytes containing the active ingredient, and immunologically-based formulations.

Suitable pharmaceutical compositions and dosage forms include, for example, tablets, capsules, caplets, pills, gel caps, troches, emulsions, dispersions, suspensions, solutions, syrups, granules, beads, transdermal patches, gels, powders, pellets, magmas, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

The pharmaceutical composition of this invention can be administered orally to a patient in any orally acceptable dosage form, such as, but not limited to, capsules, tablets, aqueous suspensions or solutions. In the case of tablets for oral use, commonly used carriers include lactose and corn starch. Alternatively, a lubricant such as magnesium stearate may be added to the pharmaceutical composition. For oral administration in capsule form, useful diluents include lactose and dried corn starch. In the case of aqueous suspensions for oral use, the active ingredient "Ribociclib" is combined with emulsifying agents and suspending agents. In other embodiments, specific sweetening agents, flavoring agents or coloring agents may be added to the pharmaceutical composition for easily swallowed by a patient.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Injectable formulations may also be prepared, packaged, or sold in devices such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents.

In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

Formulations suitable for topical administration include, but are not limited to, liquid or semi liquid preparations such as liniments, lotions, oil-in-water or water-in-oil emulsions such as creams, ointments or pastes. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein. The carrier in the ointment for topical administration may be, for example, but not limited to, mineral oil, liquid vaseline, propylene glycol, polyoxyethylene, polyoxypropylene compound, emulsion wax, or water.

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, may have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

A pharmaceutical composition of the invention may be prepared, packaged, or sold in a formulation suitable for rectal administration. Such a composition may be in the form of, for example, a suppository, a retention enema preparation, and a solution for rectal or colonic irrigation. The pharmaceutical composition of the invention may further includes suitable and non-irritating excipients to prepare a suppository. The excipient is solid at ordinary room temperature and is liquid at the rectal temperature of the subject. Therefore, the suppository would dissolved in the rectal and releasing the active ingredient "Ribociclib". Specifically, excipients include coconut cream, beeswax and polyethylene glycol.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, the terms "patient", "individual" and "subject" can be used interchangeably and may refer to a human or non-human mammal. Non-human mammals include, for example, livestock and pets, such as ovine, bovine, porcine, canine, feline and murine mammals. Preferably, the subject is human.

As used herein, the terms "neutrophil", "neutrophilic leukocyte" and "neutrocyte" can be used interchangeably and may refer to a major leukocyte in mammal blood. 60 to 70% of leukocytes are neutrophils. Neutrophils play a very important role in the innate immune system. The morphology of neutrophils is irregular and often has protrusions on the periphery of the neutrophils. The cell nucleus of immature neutrophils is band-shaped or horseshoe-shaped. The cell nucleus of mature neutrophils is segmented form, and the most common form is three segments. There are many steps in the procedure of the differentiation from the myelocyte to the neutrophil. First, the myeloblasts differentiate into the promyelocytes and start to produce primary granules (also known asazurophil). Second, the promyelocytes differentiate into myelocytes which are present in the bone marrow and start to produce secondary granules (also known as specific granules). The myelocytes further differentiate into the band cells and leaving the bone marrow to enter the blood circulation and start to produce tertiary granules (also known as gelatinase granules). Finally, the band cells differentiate into the neutrophils (also known as neutrophilic granulocyte) and start to produce secretory granules. Among the granules that can be produced by mature neutrophils, the largest granule is azurophil which is about 0.3 μm. There are many substances in the granules, including myeloperoxidase (MPO), serine protease (such as proteinase 3), cathepsin G, neutrophil elastase, lysozyme, and so on. The main function of serine proteases in the granules is to break down the pathogens in the phagosome and the lysosome. Serine proteases will also be secreted to the outside of the cell to destroy foreign pathogens. Neutrophils have strong chemotaxis and phagocytosis. As the phagocytosis began, the cell membrane is disturbed and respiratory outbreaks are caused. The oxygen consumption of the cells increases, and large amounts of cytotoxic effectors such as peroxides and superoxides are produced, which have killing activity against pathogens. In addition to using phagocytosis and secreted proteins to kill the pathogens, when the pathogens invade, neutrophils can release their own DNA to encapsulate pathogens. The said DNA is reticulated. The reticulated DNA and some enzymes originally attached to the cell nucleus then moved and attached to the DNA (for example, myeloperoxidase and neutrophil elastase) are used to encapsulate pathogens. At the same time, DNA attached to the pathogens by the negative charge of DNA. Finally, the enzyme is used to kill the pathogens. The aforementioned mechanism is called neutrophil extracellular traps (NETs). Thus, the myeloperoxidase and elastase which are produced by neutrophils are associated to the neutrophil activity. When neutrophils are over-activated, excessive oxidative stress, excessive release of granule substances, and formation of excessive NETs will damage cells or tissues. Therefore, over-activated of neutrophils is associated with many diseases, such as acute lung injury, acute respiratory distress syndrome, psoriasis, chronic obstructive pulmonary disease, pulmonary fibrosis, liver injury, fatty liver disease, liver fibrosis, myocardial infarction, shock, stroke, vasculitis, sepsis, inflammatory bowel disease, rheumatoid arthritis, systemic lupus erythematosus or atopic dermatitis.

As used herein, the term "effective amount" refers to the dose of Ribociclib which can inhibit PDE4 activity. In this invention, the amount of Ribociclib is from 1 μg/kg of the body weight/per day to 100 mg/kg of the body weight/per day.

Ranges: throughout this invention, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

A pharmaceutical composition of the invention is used for treating a PDE4-mediated disease in a patient. The pharmaceutical composition includes an effective amount of Ribociclib and a pharmaceutically acceptable carrier. In this embodiment, an amount of Ribociclib can be taken or weighted, and then added to a pharmaceutically acceptable carrier to prepare a pharmaceutical composition. The pharmaceutical composition is administered to the patient to achieve the efficacy of inhibiting PDE4 activity, and thus used for the treatment of a PDE4-mediated disease. In particular, Ribociclib can includes the following structure, or salt, solvate, hydrate, prodrug, enantiomer, diastereoisomer, or tautomer thereof and does not pose a limitation of the invention.

In addition, pharmaceutical compositions of this invention include, for example, but not limited to tablets, capsules, caplets, pills, gel caps, troches, emulsions, dispersions, suspensions, solutions, syrups, granules, beads, transdermal patches, gels, powders, pellets, magmas, creams, pastes, plasters, lotions, discs, suppositories, liquid sprays for nasal or oral administration, dry powder or aerosolized formulations for inhalation, compositions and formulations for intravesical administration and the like.

In this embodiment, the types of the carriers are described above, and therefore is omitted here for conciseness.

In this embodiment, the PDE4-mediated disease is, for example, but not limited to acute lung injury, acute respiratory distress syndrome, psoriasis, chronic obstructive pulmonary disease, pulmonary fibrosis, liver injury, fatty liver disease, liver fibrosis, myocardial infarction, shock, stroke, vasculitis, sepsis, inflammatory bowel disease, rheumatoid arthritis, systemic lupus erythematosus, atopic dermatitis or other diseases associated with PDE4, immune or neutrophils known by a person in the art.

In this embodiment, Ribociclib is used to treat the PDE4-mediated disease by inhibiting neutrophils activity.

In this embodiment, Ribociclib is used to treat the PDE4-mediated disease by inhibiting PDE4A activity, PDE4B activity, PDE4C activity or PDE4D activity of the PDE4 pathway.

In this embodiment, the effective amount of Ribociclib is from 1 μg/kg of the body weight/per day to 100 mg/kg of the body weight/per day. Preferably, the effective amount of Ribociclib is 1 µg, 5 µg, 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 105 µg, 110 µg, 115 µg, 120 µg, 125 µg, 130 µg, 135 µg, 140 µg, 145 µg, 150 µg, 155 µg, 160 µg, 165 µg, 170 µg, 175 µg, 180 µg, 185 µg, 190 µg, 195 µg, 200 µg, 205 µg, 210 µg, 215 µg, 220 µg, 225 µg, 230 µg, 235 µg, 240 µg, 245 µg, 250 µg, 255 µg, 260 µg, 265 µg, 270 µg, 275 µg, 280 µg, 285 µg, 290 µg, 295 µg, 300 µg, 305 µg, 310 µg, 315 µg, 320 µg, 325 µg, 330 µg, 335 µg, 340 µg, 345 µg, 350 µg, 355 µg, 360 µg, 365 µg, 370 µg, 375 µg, 380 µg, 385 µg, 390 µg, 395 µg, 400 µg, 405 µg, 410 µg, 415 µg, 420 µg, 425 µg, 430 µg, 435 µg, 440 µg, 445 µg, 450 µg, 455 µg, 460 µg, 465 µg, 470 µg, 475 µg, 480 µg, 485 µg, 490 µg, 495 µg, 500 µg, 505 µg, 510 µg, 515 µg, 520 µg, 525 µg, 530 µg, 535 µg, 540 µg, 545 µg, 550 µg, 555 µg, 560 µg, 565 µg, 570 µg, 575 µg, 580 µg, 585 µg, 590 µg, 595 µg, 600 µg, 605 µg, 610 µg, 615 µg, 620 µg, 625 µg, 630 µg, 635 µg, 640 µg, 645 µg, 650 µg, 655 µg, 660 µg, 665 µg, 670 µg, 675 µg, 680 µg, 685 µg, 690 µg, 695 µg, 700 µg, 705 µg, 710 µg, 715 µg, 720 µg, 725 µg, 730 µg, 735 µg, 740 µg, 745 µg, 750 µg, 755 µg, 760 µg, 765 µg, 770 µg, 775 µg, 780 µg, 785 µg, 790 µg, 795 µg, 800 µg, 805 µg, 810 µg, 815 µg, 820 µg, 825 µg, 830 µg, 835 µg, 840 µg, 845 µg, 850 µg, 855 µg, 860 µg, 865 µg, 870 µg, 875 µg, 880 µg, 885 µg, 890 µg, 895 µg, 900 µg, 905 µg, 910 µg, 915 µg, 920 µg, 925 µg, 930 µg, 935 µg, 940 µg, 945 µg, 950 µg, 955 µg, 960 µg, 965 µg, 970 µg, 975 µg, 980 µg, 985 µg, 990 µg, 995 µg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg, 20.5 mg, 21 mg, 21.5 mg, 22 mg, 22.5 mg, 23 mg, 23.5 mg, 24 mg, 24.5 mg, 25 mg, 25.5 mg, 26 mg, 26.5 mg, 27 mg, 27.5 mg, 28 mg, 28.5 mg, 29 mg, 29.5 mg, 30 mg, 30.5 mg, 31 mg, 31.5 mg, 32 mg, 32.5 mg, 33 mg, 33.5 mg, 34 mg, 34.5 mg, 35 mg, 35.5 mg, 36 mg, 36.5 mg, 37 mg, 37.5 mg, 38 mg, 38.5 mg, 39 mg, 39.5 mg, 40 mg, 40.5 mg, 41 mg, 41.5 mg, 42 mg, 42.5 mg, 43 mg, 43.5 mg, 44 mg, 44.5 mg, 45 mg, 45.5 mg, 46 mg, 46.5 mg, 47 mg, 47.5 mg, 48 mg, 48.5 mg, 49 mg, 49.5 mg, 50 mg, 50.5 mg, 51 mg, 51.5 mg, 52 mg, 52.5 mg, 53 mg, 53.5 mg, 54 mg, 54.5 mg, 55 mg, 55.5 mg, 56 mg, 56.5 mg, 57 mg, 57.5 mg, 58 mg, 58.5 mg, 59 mg, 59.5 mg, 60 mg, 60.5 mg, 61 mg, 61.5 mg, 62 mg, 62.5 mg, 63 mg, 63.5 mg, 64 mg, 64.5 mg, 65 mg, 65.5 mg, 66 mg, 66.5 mg, 67 mg, 67.5 mg, 68 mg, 68.5 mg, 69 mg, 69.5 mg, 70 mg, 70.5 mg, 71 mg, 71.5 mg, 72 mg, 72.5 mg, 73 mg, 73.5 mg, 74 mg, 74.5 mg, 75 mg, 75.5 mg, 76 mg, 76.5 mg, 77 mg, 77.5 mg, 78 mg, 78.5 mg, 79 mg, 79.5 mg, 80 mg, 80.5 mg, 81 mg, 81.5 mg, 82 mg, 82.5 mg, 83 mg, 83.5 mg, 84 mg, 84.5 mg, 85 mg, 85.5 mg, 86 mg, 86.5 mg, 87 mg, 87.5 mg, 88 mg, 88.5 mg, 89 mg, 89.5 mg, 90 mg, 90.5 mg, 91 mg, 91.5 mg, 92 mg, 92.5 mg, 93 mg, 93.5 mg, 94 mg, 94.5 mg, 95 mg, 95.5 mg, 96 mg, 96.5 mg, 97 mg, 97.5 mg, 98 mg, 98.5 mg, 99 mg, 99.5 mg or 100 mg/kg of the body weight/per day. Of course, the effective amount of Ribociclib may be any value and range encompassed between any two values within the foregoing ranges and may be changed according to the carrier which is used, the route of administration, or the individual who in need and the physiology state thereof.

This invention also provides a pharmaceutical composition for use in the treatment of a PDE4-mediated disease in a patient. This invention further provides a pharmaceutical composition for inhibiting PDE4 activity. This invention further provides a pharmaceutical composition for use in inhibiting PDE4 activity. In addition, this invention provides a method for treating a PDE4-mediated disease in a patient. The method includes providing a pharmaceutical composition comprising an effective amount of Ribociclib and a pharmaceutically acceptable carrier. Ribociclib is used to treat the PDE4-mediated disease by inhibiting PDE4 activity. The PDE4-mediated disease is acute lung injury, acute respiratory distress syndrome, psoriasis, chronic obstructive pulmonary disease, pulmonary fibrosis, liver injury, fatty liver disease, liver fibrosis, myocardial infarction, shock, stroke, vasculitis, sepsis, inflammatory bowel disease, rheumatoid arthritis, systemic lupus erythematosus or atopic dermatitis. The concentration or amount of the pharmaceutical composition, the types of the carriers, and other properties are mostly the same as those of the pharmaceutical composition described above, and therefore is omitted here for conciseness.

As mentioned above, the pharmaceutical composition of this invention and use thereof can inhibit PDE4 activity in a patient for avoiding the effect of PDE4 to the function of the immune system, and thus achieves the efficacy of treating PDE4-mediated diseases.

Example 1: The Results of Ribociclib Specifically Inhibiting PDE4 Activity

Enzymatic activities of PDE subtypes were analyzed according to the user manual of HTRF® package insert cAMP dynamic tests (Cisbio bioassays, catalog number 62AM$_4$PEB). Ribociclib was dissolved in DMSO (as solvent) and then added to PDE assay buffer which contains PDE4A, PDE4B, PDE4C, PDE4D, PDE3B or PDE7A (sold by BPS bioscience). The final concentration of Ribociclib was 0.1 to 30 µM. Then, the mixtures were incubated for 10 minutes at 37° C. PDE assay buffer which was added by DMSO (solvent, marked as "–" in FIGS. 1A-1F) instead of Ribociclib was as a control in this experiment. 60 nM of cAMP was added to each reagent and then incubated for 45 minutes at 37° C. After incubation, cAMP-d$_2$ and anti-cAMP-cryptate were added to each reagent and react at room temperature for 1 hour away from light. Finally, the reagents were quantified by the luminometer (TECAN infinite 200 Pro) to detect enzymatic activities of PDE subtypes. The results were shown in FIGS. 1A to 1F.

Figure 1A:
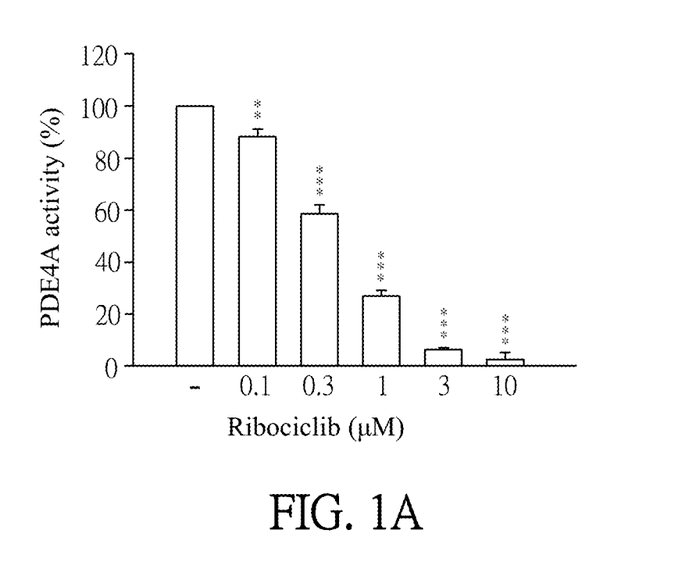
FIG. 1A shows a result of PDE4A activity inhibited by the different amount of Ribociclib.
Figure 1B:
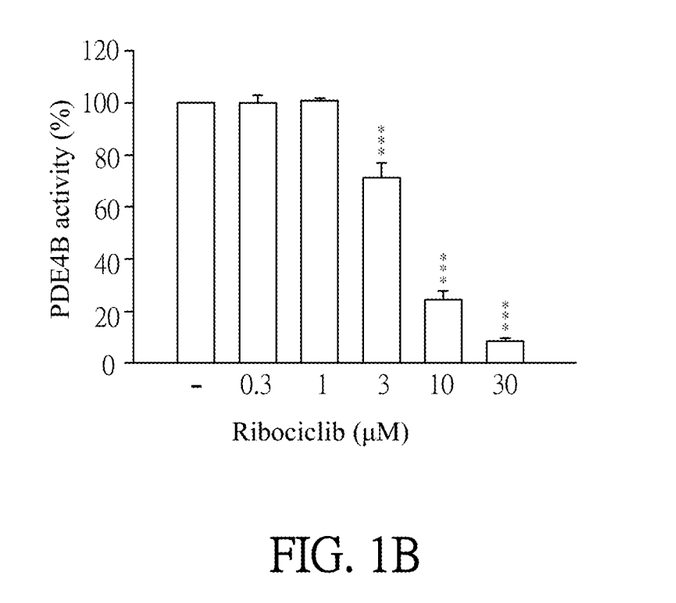
FIG. 1B shows a result of PDE4B activity inhibited by the different amount of Ribociclib.
Figure 1C:
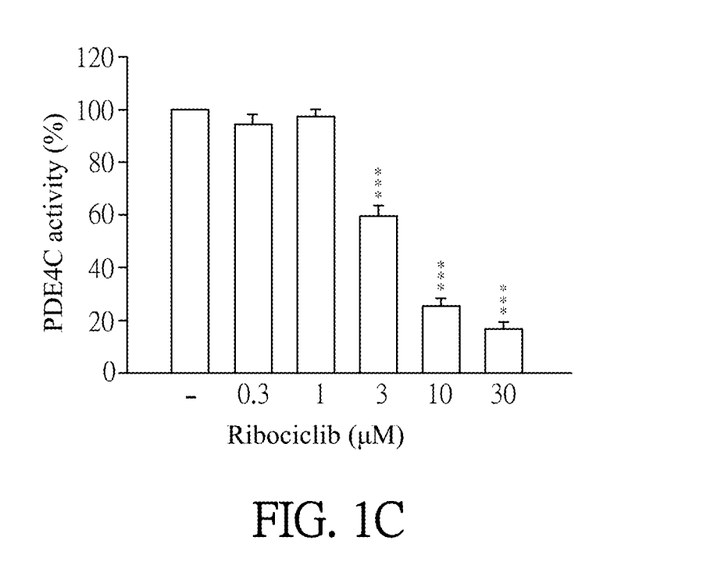
FIG. 1C shows a result of PDE4C activity inhibited by the different amount of Ribociclib.
Figure 1D:
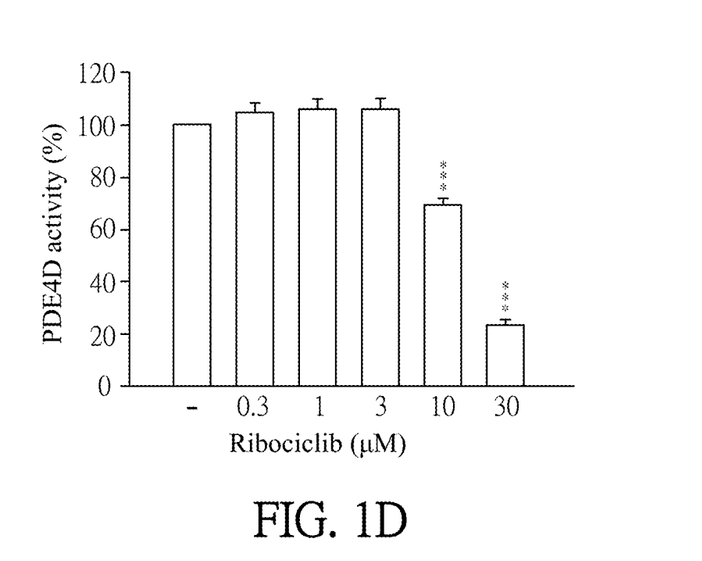
FIG. 1D shows a result of PDE4D activity inhibited by the different amount of Ribociclib.
Figure 1E:
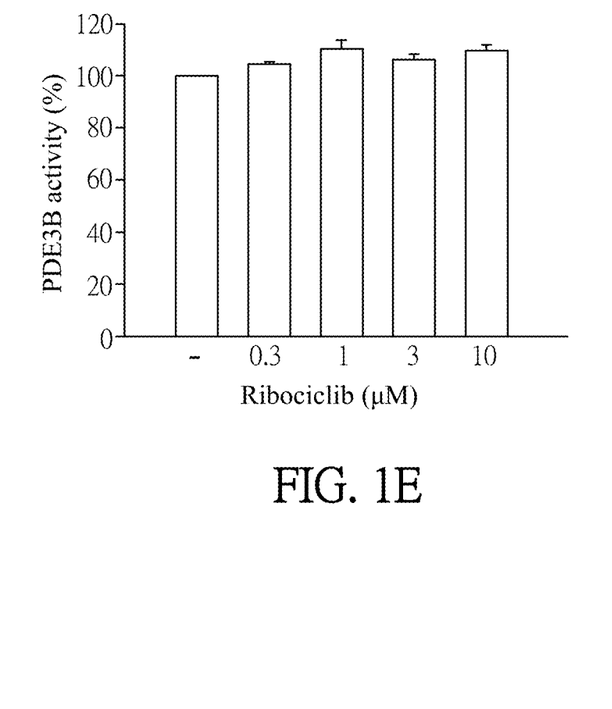
FIG. 1E shows a result that phosphodiesterase 3B (PDE3B) activity would not be inhibited by the different amount of Ribociclib.
Figure 1F:
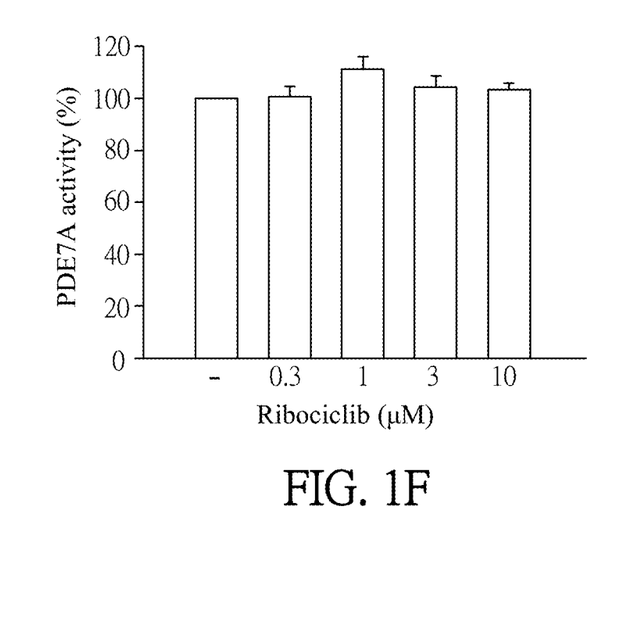
FIG. 1F shows a result that phosphodiesterase 7A (PDE7A) activity would not be inhibited by the different amount of Ribociclib.

Please refer to FIGS. 1A to 1F. FIG. 1A shows a result of PDE4A activity inhibited by the different amount of Ribociclib. FIG. 1B shows a result of PDE4B activity inhibited by the different amount of Ribociclib. FIG. 1C shows a result of PDE4C activity inhibited by the different amount of Ribociclib inhibit. FIG. 1D shows a result of PDE4D activity inhibited by the different amount of Ribociclib. FIG. 1E shows a result that the different amount of Ribociclib would not inhibit PDE3B activity. FIG. 1F shows a result that the different amount of Ribociclib would not inhibit PDE7A activity. As shown in FIGS. 1A-1F, Ribociclib specifically inhibits phosphodiesterase 4 activity except the control (marked as "–"). In more detailed, as shown in FIG. 1A, 0.1 µM, 0.3 µM, 1 µM, 3 µM and 10 µM of Ribociclib significantly inhibit PDE4A activity. PDE4A activity is significantly decreased along with increasing the concentration of Ribociclib. As shown in FIG. 1B, 3 µM, 10 µM and 30 µM of Ribociclib significantly inhibit PDE4B activity. PDE4B activity is significantly decreased along with the increase of concentration of Ribociclib. As shown in FIG. 1C, 3 µM, 10 µM and 30 µM of Ribociclib significantly inhibit PDE4C activity. PDE4C activity is significantly decreased along with increasing the concentration of Ribociclib. As shown in FIG. 1D, 10 μM and 30 μM of Ribociclib significantly inhibit PDE4D activity. PDE4D activity is significantly decreased along with increasing the concentration of Ribociclib. As shown in FIGS. 1E and 1F, Ribociclib would not inhibit PDE3B and PDE7A activity. The results show that Ribociclib specifically inhibits phosphodiesterase 4 activity. As shown in FIGS. 1A-1F, "−" is control;  is p<0.01 compared with control; * is p<0.001 compared with control. All data are expressed as mean±standard error of the mean (SEM) (n=6); error bar presents SEM.

Example 2: Ribociclib Restricts Superoxide Anion Generation in the fMLF-Stimulated Neutrophils Donors:

Donors were healthy individuals aged between 20 to 35 years old who have no any known diseases or risk factors and had normal work-rest cycles and did not take medicine for more than one week. The informed consent to participate which was approved by the Institutional Review Board are signed by the donors. 50 mL of blood was collected from the median cubital vein of each donor by sterile vacutainer, and was used to isolate neutrophils for the following experiments.

Figure 2:
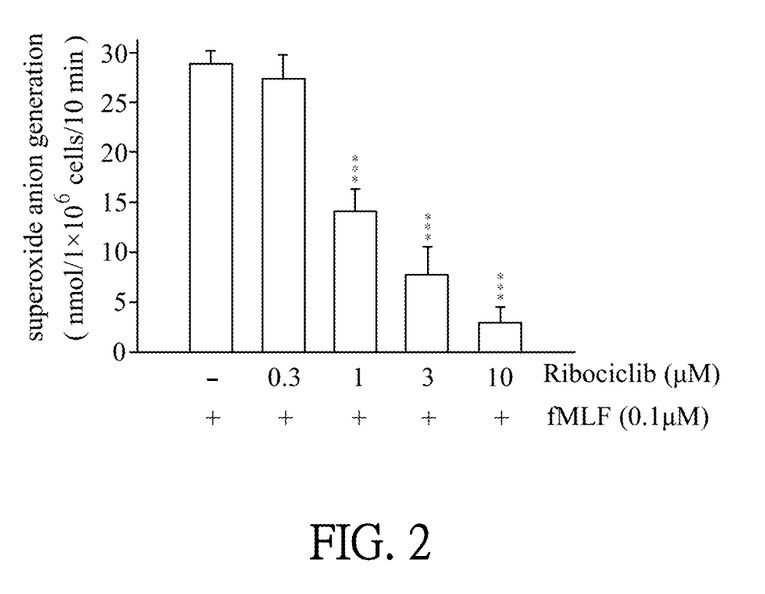
FIG. 2 shows a result that Ribociclib restricts superoxide anion generation in the formyl-Met-Leu-Phe (fMLF)-stimulated neutrophils.

Human neutrophils (isolated from whole blood of donors) were incubated with DMSO (as solvent, marked as "−" in the groups at X-axis in FIGS. 2A and 2B) or Ribociclib (0.3-10 μM) for 5 minutes, and then stimulated the neutrophils with or without fMLF (0.1 μM)/cytochalasin B (CB, 1 μg/ml) for another 10 minutes to activate the neutrophils. The absorbance ($OD_{550}$) of the reaction mixture was then measured by a spectrophotometer at OD 550 nm. The reading of $OD_{550}$ is used to detect the reduction of ferricytochrome c, which indicates the amount of superoxide anion. Cytochalasin B was sold by Sigma-Aldrich, catalog number #2506; fMLF was sold by Sigma-Aldrich, catalog number #454454; model number of the spectrophotometer is HITACHI U-3010.

Please refer to FIG. 2, FIG. 2 shows a result that Ribociclib restricts superoxide anion generation in the fMLF-stimulated neutrophils. As shown in FIG. 2, the group which is incubated with DMSO (instead of Ribociclib) and then stimulated with fMLF is played as the control in this experiment. Compared with the control, the group which is incubated with Ribociclib and then stimulated by fMLF can restrict the generation of superoxide anion, and the groups of adding 1 μM, 3 μM and 10 μM of Ribociclib significantly restrict the generation of superoxide anion. Moreover, the generation of superoxide anion is significantly decreased along with increasing the concentration of Ribociclib. This result showing that Ribociclib inhibits neutrophils activity. As shown in FIG. 2, "−" is without Ribociclib (added DMSO); "+" is added; ***p<0.001 compared with the control. All data are expressed as mean±SEM (n=6); error bar presents SEM.

Example 3: Preparation of the Pharmaceutical Composition

250 μg or 500 μg of Ribociclib was dissolved in 50 μl of 0.5% (w/v) methylcellulose 400 solution to make a pharmaceutical composition. The Ribociclib concentration of the pharmaceutical composition was 250 μg/50 μl or 500 μg/50 μl and used in the subsequent animal experimental examples 4 and 5.

Example 4: Ribociclib Reducing the Psoriasis-Like Symptoms in the IMQ-Treated Mice Male BALB/c mice (7-9 weeks of age, the body weight of each mouse is about 25 g) were divided into different groups, and each group has 6 mice. Each mouse was epilation on the back and then treated with 50 μl of solvent (0.5% methylcellulose 400) or 50 μl of the pharmaceutical composition prepared in example 3 (the concentration of Ribociclib is 10 or 20 mg/kg of body weight) by applying on the nude back skin before topical treatment of imiquimod (IMQ, sold by 3M Health Care Limited). And then applying with or without IMQ on the nude back skin of mice to cause psoriasis-like symptom. Each treatment was given once per day for 5 consecutive days. The mice which applying solvent and IMQ is played as the control. The mice which merely applying solvent is played as the blank.

Figure 3:
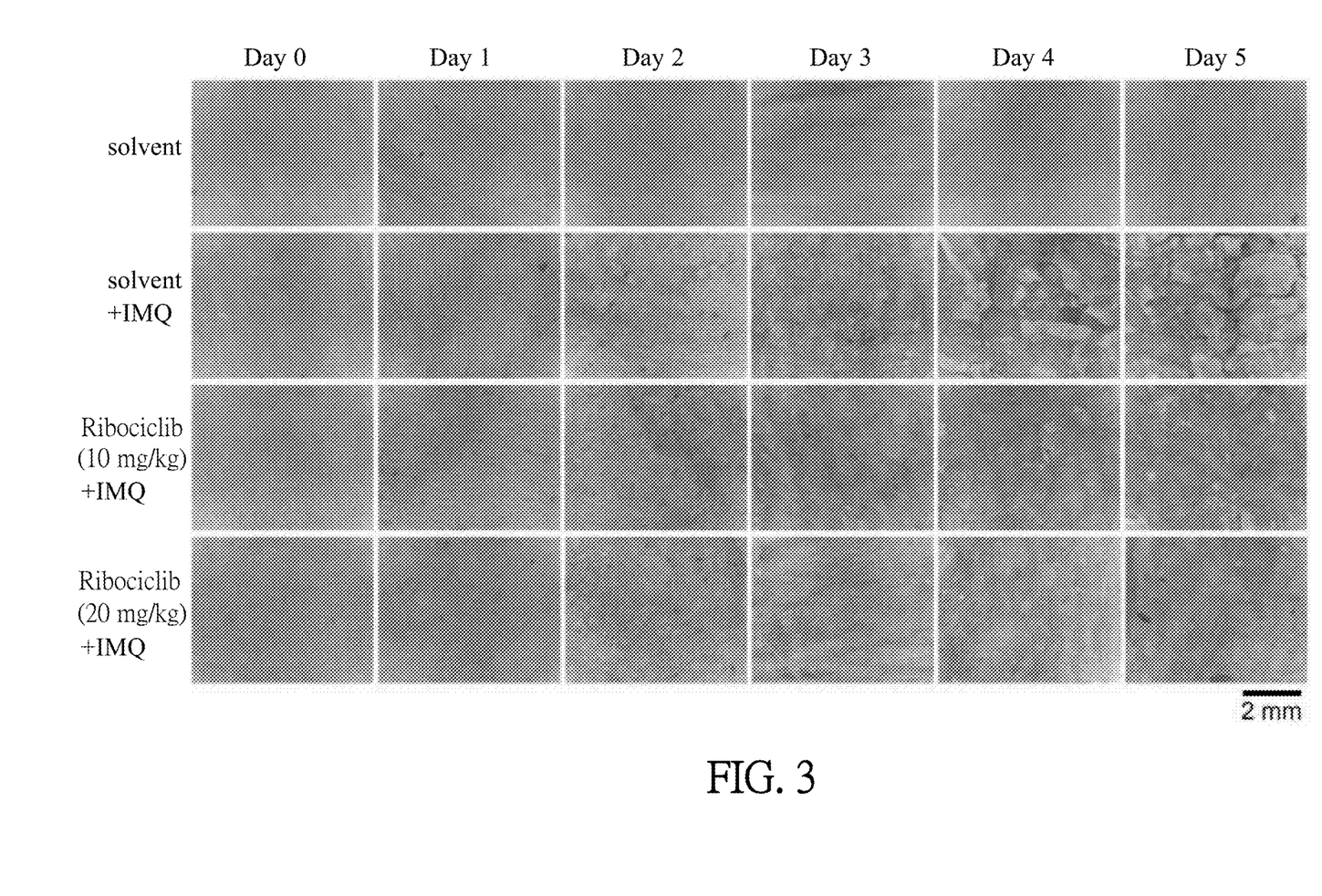
FIG. 3 shows a result that Ribociclib reduce the psoriasis-like symptoms in imiquimod (IMQ)-treated mice.

Please refer to FIG. 3, FIG. 3 shows a result that Ribociclib reduces the psoriasis-like symptoms in the IMQ-treated mice. FIG. 3 shows the partially enlarged photos of mice skin after 0 to $5^{th}$ day treating by different treatments. The photos of FIG. 3 were taken by handheld digital microscope. As shown in FIG. 3, the group merely treated by solvent without IMQ did not cause psoriasis-like symptoms during 5 days after the treatments. The control group treated by solvent and IMQ start to cause psoriasis-like symptoms after the treatment in $3^{rd}$ day. Compared with the control, the psoriasis-like symptoms were not observed in the group treated by Ribociclib and IMQ after the treatment in $5^{th}$ day. Both 10 mg/kg of the body weight and 20 mg/kg of the body weight of Ribociclib can improve or cure the psoriasis-like symptoms. The result of this example indicates that Ribociclib can improve or cure the psoriasis-like symptom.

Example 5: Ribociclib Attenuating the Acute Lung Injury in the LPS-Treated Mice

Acute lung injury (ALI) was induced by intra-tracheal spray of 2 mg/kg LPS in seven to eight weeks old BALB/c mice. Mice were fasted overnight and then intravenously injected with 50 μl of the pharmaceutical composition prepared in example 3 (Ribociclib concentration is 10 or 20 mg/kg of body weight) or an equal volume of solvent (50 μl of 0.5% methylcellulose 400). After 1 hour, mice were performed under anesthesia and then instilled with an intra-tracheal spray of 2 mg/kg LPS (dissolved in 40 μl 0.9% saline) or 0.9% saline. Five hours later, mice were sacrificed and the lungs were collected. The lungs were fixed in 10% formalin for tissue section. The lung sections were stained with hematoxylin and eosin (H&E) by IHC. The result is shown in FIG. 4.

Figure 4:
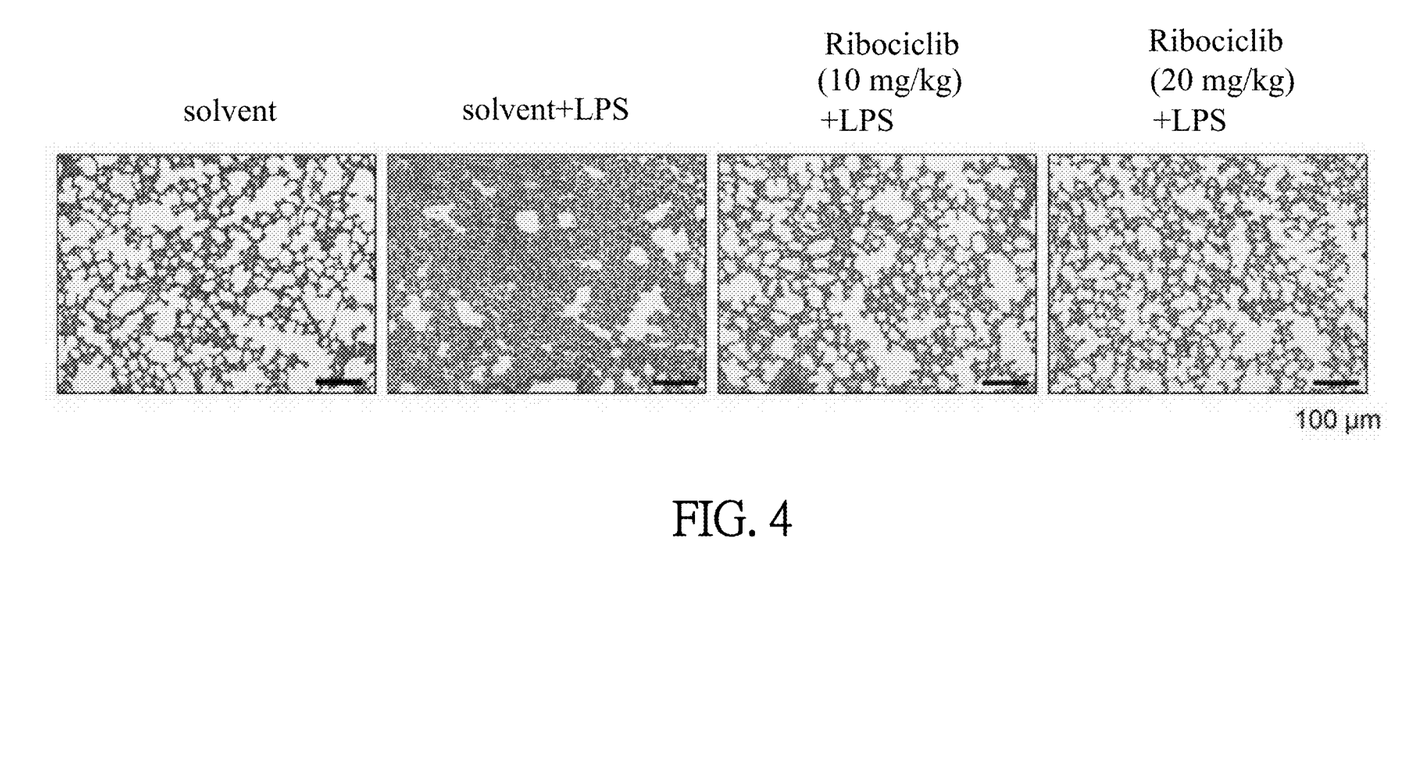
FIG. 4 shows a result that Ribociclib attenuates the acute lung injury in LPS-treated mice.

Please refer to FIG. 4, FIG. 4 shows a result that Ribociclib attenuates the acute lung injury in the LPS-treated mice. FIG. 4 shows the lung tissue section photos of mice treating by different treatments. The lung tissue sections were stained by H&E. The lung tissue of mice which merely treated by solvent did not cause acute lung injury. The lung tissue of mice which treated by solvent and then LPS is played as the control. The lung tissue of the control is observed that neutrophils infiltration and morphology change. Therefore, the control group has caused acute lung injury. Compared to the control, the neutrophils infiltration and morphology change were not observed in the lung tissue of mice which treated by Ribociclib and then LPS. Therefore, this group did not cause acute lung injury. This result indicates that Ribociclib can improve or cure the acute lung injury.

According to the result of example 1, the pharmaceutical composition of this invention may significantly and specifically inhibits phosphodiesterase 4 activity (including PDE4A, PDE4B, PDE4C and PDE4D). According to the result of example 2, the pharmaceutical composition of this invention may significantly inhibit neutrophils activity. According to the result of example 4, the pharmaceutical composition of this invention may improve or cure the psoriasis-like symptoms. According to the result of example 5, the pharmaceutical composition of this invention may improve or cure the acute lung injury. The examples are described for illustration but not intended to be limiting.

As mentioned above, the pharmaceutical composition and use of this invention can inhibit PDE4 activity and neutrophils activity in a patient for avoiding the effect of PDE4 and neutrophils to the function of the immune system, and thus achieves the efficacy of treating PDE4-mediated diseases.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A method for treating acute lung injury in a patient, the method comprises administering an effective amount of Ribociclib to the patient.

2. The method according to claim 1, wherein Ribociclib is used to treat acute lung injury by inhibiting PDE4A activity, PDE4B activity, PDE4C activity or PDE4D activity of a PDE4 pathway.

3. The method according to claim 1, wherein Ribociclib is administered to the patient from 1 μg/kg of the body weight/per day to 100 mg/kg of the body weight/per day.

* * * * *